(12) United States Patent
Long et al.

(10) Patent No.: US 9,918,468 B2
(45) Date of Patent: Mar. 20, 2018

(54) COMPOSITIONS AND METHODS FOR CONTROLLING WEEDS IN CROPS

(71) Applicant: FMC Corporation, Philadelphia, PA (US)

(72) Inventors: Mitchell Long, Saskatoon (CA); James Betts, Sparks, GA (US); David Strilchuk, Regina (CA)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 14/939,556

(22) Filed: Nov. 12, 2015

(65) Prior Publication Data

US 2016/0135454 A1    May 19, 2016

Related U.S. Application Data

(60) Provisional application No. 62/079,682, filed on Nov. 14, 2014.

(51) Int. Cl.
| | | |
|---|---|---|
| *A01N 57/00* | (2006.01) | |
| *A01N 57/04* | (2006.01) | |
| *A01N 37/40* | (2006.01) | |
| *A01N 43/653* | (2006.01) | |
| *A01N 57/20* | (2006.01) | |

(52) U.S. Cl.
CPC .......... *A01N 37/40* (2013.01); *A01N 43/653* (2013.01); *A01N 57/20* (2013.01)

(58) Field of Classification Search
None
See application file for complete search history.

(56) References Cited

U.S. PATENT DOCUMENTS

| | | | | |
|---|---|---|---|---|
| 2008/0132414 A1* | 6/2008 | Zawierucha | ......... | A01N 43/653 504/128 |
| 2011/0224077 A1* | 9/2011 | Hacker | ................. | A01N 57/20 504/103 |
| 2014/0031214 A1* | 1/2014 | Yerkes | .................. | A01N 43/40 504/103 |
| 2014/0155265 A1 | 6/2014 | Porter | | |
| 2014/0162879 A1 | 6/2014 | Ovalle et al. | | |

FOREIGN PATENT DOCUMENTS

| | | | |
|---|---|---|---|
| CA | 2008175 A1 | | 7/1991 |
| CA | 2347774 | | 5/2000 |
| CN | 102326558 | * | 1/2012 |
| CN | 102326558 A | | 1/2012 |
| WO | 2005077178 | | 8/2005 |

OTHER PUBLICATIONS

Colby S.R "Calculating Synergistic and Antagonistic Responses of Herbicide Combinations" Weeds 15, pp. 20-22.
2014 Pre-Seed Control Options (http://www.shur-gro.ca/2014-pre-seed-control-options).
Pyraflufen-Ethyl Evaluation Report ERC2014-03 published Oct. 23, 2014 by the Health Canada Pest Management Regulatory Agency.
The Pesticide Manual, 2009, fifteen edition, published by BCPC; Editor: CDS Tomlin.

* cited by examiner

*Primary Examiner* — Alton Pryor
(74) *Attorney, Agent, or Firm* — FMC Corporation

(57) ABSTRACT

Compositions and methods for controlling volunteer crop weeds in a crop by applying to weeds a herbicidally effective amount of a synergistic herbicidal composition that includes bromoxynil and a protoporphyrinogen oxidase (PPO) inhibitor are disclosed.

15 Claims, No Drawings

COMPOSITIONS AND METHODS FOR CONTROLLING WEEDS IN CROPS

FIELD OF THE DISCLOSED SUBJECT MATTER

The presently disclosed subject matter relates to compositions containing bromoxynil and protoporphyrinogen oxidase (PPO) inhibitors, and methods for controlling volunteer or herbicide resistant crop weeds using those compositions.

BACKGROUND

One of the more preferred methods of controlling weeds in crops involves the post-emergent control of weeds wherein herbicide(s) are applied after the crop in question has emerged from the soil. Post-emergent control is desirable as it requires the application of herbicide only where an infestation of weeds is present. In contrast, pre-emergent control requires the application of herbicide early in the growing season before most weeds have germinated, with the result that such chemicals must be employed throughout a field even if they would ultimately not be needed.

There are approximately 20 million acres of canola grown in western Canada. At harvest canola crops leave an average of 2-3 bushels per acre of seed in the field, or at least 20 times the normal seeding rate. Canola seed can remain viable in the soil for 2 to 3 years, and with shortened crop rotations, volunteer canola has become a major weed pest in crops, including canola crops.

Bromoxynil (3,5-dibromo-4-hydroxybenzonitrile), is an effective post-emergent herbicide for a number of weeds, particularly broadleaf weeds, including volunteer canola.

Protoporphyrinogen oxidase (PPO) is an enzyme found in both plants and animals, which is responsible for the seventh step in the biosynthesis of protoporphyrin IX. This porphyrin is the biosynthetic precursor of hemoglobin in animals and chlorophyll in plants. The enzyme catalyzes the dehydrogenation of protoporphyrinogen IX to form protoporphyrin IX.

Protoporphyrinogen oxidase inhibitors are herbicides that act by blocking the production of chlorophyll and heme in a plant, causing an accumulation of protoporphyrinogen IX that is ultimately toxic to the plant.

A majority of the canola planted in Canada and the USA has been genetically modified to be tolerant to glyphosate or glufosinate. Therefore these herbicides, when used as a burn down treatment on a field prior to seeding with canola seed, fail to control canola weeds. A solution to this problem is described herein.

SUMMARY OF THE DISCLOSED SUBJECT MATTER

It has now been discovered that bromoxynil, when used in combination with a Protoporphyrinogen oxidase (PPO) inhibitor, is surprisingly effective at controlling broadleaf weeds, showing synergism with regard to volunteer crop weed control, including canola which are resistant to glyphosate and glufosinate.

The purpose and advantages of the disclosed subject matter will be set forth in, and apparent from, the description that follows, as well as will be learned by practice of the disclosed subject matter. Additional advantages of the disclosed subject matter will be realized and attained by the methods and compositions particularly pointed out in the written description and claims hereof.

One aspect of the invention is directed to a method of selectively controlling glyphosate- or glufosinate-resistant weed or glyphosate- or glufosinate-resistant volunteer crop weeds in a crop, comprising applying to the volunteer crop weeds a herbicidally effective amount of a herbicidal composition comprising bromoxynil and a protoporphyrinogen oxidase (PPO) inhibitor. In one embodiment, the PPO inhibitor is selected from the group consisting of carfentrazone, carfentrazone-ethyl, sulfentrazone, fluthiacet-methyl, saflufenacil, and mixtures of two or more thereof; and is preferably selected from carfentrazone or carfentrazone-ethyl. More preferably the PPO inhibitor comprises carfentrazone-ethyl.

In one embodiment of the method, the herbicidal composition is applied to the field when the volunteer crop weeds are in the 1-6 leaf stage. Volunteer crop weeds can be selected from the group consisting of canola, genetically modified canola, soybean and genetically modified soybean. The crop containing these volunteer crop weeds can be selected from the group consisting of genetically modified and non-modified corn, wheat, oat, rye, soybean, cotton, flax, jute, rape, canola, linseed, sesame, safflower, sunflower, clover, beet, sugar beet, sorghum, millet, rice, peanut, pea, bean, cucumber, pepper, melon, cabbage, onion, squash, lettuce, asparagus, eggplant, tomato, tobacco, flower seed and turfgrass. In one embodiment the crop is selected from the group consisting of canola, genetically modified canola, and mixtures thereof, and the volunteer crop weed is selected from the group consisting of canola, genetically modified canola and mixtures thereof. In one embodiment the crop is glyphosate- or glufosinate-resistant canola, and the volunteer crop weed is glyphosate- or glufosinate-resistant canola.

In one embodiment of the method the herbicidal composition is applied to a field as a burn down treatment in order to eliminate the emerged weeds, including volunteer crop weeds, prior to seeding the desired crop which crop may include genetically modified or non-modified corn, wheat, oat, rye, soybean, cotton, flax, jute, rape, canola, linseed, sesame, safflower, sunflower, clover, beet, sugar beet, sorghum, millet, rice, peanut, pea, bean, cucumber, pepper, melon, cabbage, onion, squash, lettuce, asparagus, eggplant, tomato, tobacco, flower seed and turfgrass.

In one embodiment of the method the applied composition comprises a tank mix of formulated bromoxynil and a formulated protoporphyrinogen oxidase (PPO) inhibitor. In one embodiment the PPO inhibitor is carfentrazone-ethyl. In one embodiment the tank mix further comprises glyphosate or glufosinate.

In one embodiment the applied rate of bromoxynil and/or the applied rate of the protoporphyrinogen oxidase inhibitor is less than the labeled or registered application rate for control of the crop represented by the volunteer crop weed. In one embodiment the applied rate of bromoxynil and the applied rate of carfentrazone-ethyl are each half of their registered rates for control of the crop represented by the volunteer crop weed.

In one embodiment of the method, the applied composition provides synergistic control of the volunteer crop weed. In one embodiment, control of the volunteer crop weed is effective through at least 21 days post treatment.

Another aspect of the invention is directed to a synergistic herbicidal composition comprising bromoxynil and a protoporphyrinogen oxidase inhibitor (PPO) in a ratio between about 4:1 and about 16:1 by weight, wherein application of an effective amount of the synergistic herbicidal composition is effective to selectively control volunteer crop weeds in a crop. In one embodiment the synergistic herbicidal composition further comprises glyphosate or glufosinate. In one embodiment the PPO inhibitor is selected from the group consisting of carfentrazone, carfentrazone-ethyl, sulfentrazone, fluthiacet-methyl, saflufenacil, and mixtures of two or more thereof. In one embodiment the protoporphyrinogen oxidase inhibitor comprises carfentrazone-ethyl. In one embodiment the synergistic herbicidal composition comprises carfentrazone-ethyl and further comprises glyphosate.

DETAILED DESCRIPTION

The present document discloses compositions and methods that provide synergistic efficacy for controlling crop weeds in crops. This includes one of the most problematic weeds in Canadian agriculture, volunteer canola. The compositions and methods disclosed herein are advantageous in that this synergistic combination now provides a new tool to control crop weeds which are resistant to glyphosate and glufosinate due to genetic modification.

One aspect of the invention is directed to a method of selectively controlling glyphosate- or glufosinate-resistant volunteer crop weeds in a crop, comprising applying to the volunteer crop weeds a herbicidally effective amount of a herbicidal composition comprising bromoxynil and a protoporphyrinogen oxidase (PPO) inhibitor. In one embodiment, the PPO inhibitor is selected from the group consisting of carfentrazone, carfentrazone-ethyl, sulfentrazone, fluthiacet-methyl, saflufenacil, and mixtures of two or more thereof. In a preferred embodiment the PPO inhibitor comprises carfentrazone or carfentrazone-ethyl. In a more preferred embodiment the PPO inhibitor comprises carfentrazone-ethyl.

In another embodiment, the protoporphyrinogen oxidase (PPO) inhibitor is selected from diphenyl ethers, oxadiazoles, cyclic imides or pyrazoles. Examples of these PPO classes include, without limitation, acifluorfen, acifluorfen-sodium, azafenidin, bifenox, butafenacil, chlomethoxyfen, chlornitrofen, ethoxyfen-ethyl, fluorodifen, fluoroglycofen-ethyl, fluoronitrofen, fomesafen, furyloxyfen, halosafen, lactofen, nitrofen, nitrofluorfen, oxyfluorfen, flumiclorac-pentyl, flumioxazine, profluazol, pyrazogyl, oxadiargyl, oxadiazon, pentoxazone, fluazolate, pyraflufen-ethyl, benzfendizone, butafenacil, cinidon-ethyl, flumipropyn, flupropacil, fluthiacet-methyl, thidiazimin, azafenidin, carfentrazone, carfentrazone-ethyl, sulfentrazone, saflufenacil, flufenpyr-ethyl, ET-751, JV 485, nipyraclofen, or mixtures of two or more thereof. Preferably the PPO inhibitors are selected from the group consisting of carfentrazone, sulfentrazone, fluthiacet-methyl, saflufenacil, and mixtures of two or more thereof. More preferably the PPO inhibitor comprises carfentrazone, still more preferably carfentrazone-ethyl.

The herbicidal compositions of the present disclosure can be in any conventional agriculturally useful form, for example, in the form of a twin pack, or in a ready-to-use formulation, or in the form of a tank mix. Additionally, the active compounds can be supplied (either separately or pre-mixed) in any appropriate formulation type, for example an emulsion concentrate (EC), a suspension concentrate (SC), a suspo-emulsion (SE), a capsule suspension (CS), a water dispersible granule (WG), an emulsifiable granule (EG), a water in oil emulsion (EO), an oil in water emulsion (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a dispersible concentrate (DC), a wettable powder (WP), a mixed heterogeneous formulation of CS and EW (ZW), or any other technically feasible formulation in combination with agriculturally acceptable adjuvants. For tank mixing, commercial formulations of bromoxynil and a PPO inhibitor are combined in a tank prior to application, in the appropriate ratio to provide the targeted weight ratio of the active ingredients. In one embodiment, the herbicidal compositions of the present disclosure are tank mixes. In another embodiment, the herbicidal compositions of the present disclosure are supplied as premix emulsifiable concentrates (ECs).

Rates of application of the composition, or tank-mixed separately formulated active ingredients, will vary according to prevailing conditions such as targeted volunteer crop weeds, degree of infestation, weather conditions, soil conditions, crop species, mode of application, and application time. Compositions containing bromoxynil and a PPO inhibitor can be applied as sprays, such as water-dispersible concentrates, wettable powders, or water-dispersible granules. In one embodiment, the rate of application for active ingredient ("ai") (e.g. bromoxynil and a PPO inhibitor) is from about 30 g ai/acre to about 120 g ai/acre, preferably about 30 g ai/acre to about 65 g ai/acre.

In one embodiment, the present disclosure describes an agricultural formulation or tank mix containing at least two agriculturally active ingredients: bromoxynil and a PPO inhibitor. In one embodiment, the PPO inhibitor is selected from carfentrazone, carfentrazone-ethyl, sulfentrazone, fluthiacet-methyl, saflufenacil, or mixtures of two or more thereof. In another embodiment, the PPO inhibitor is preferably carfentrazone-ethyl. According to one aspect of this embodiment, the bromoxynil and the PPO inhibitor are present in a ratio between about 4:1 and about 31:1 by weight. In one embodiment, the bromoxynil and the PPO inhibitor are present in a ratio between about 4:1 and about 16:1 by weight. In a preferred embodiment, the bromoxynil and the PPO inhibitor are present in a ratio between about 5:1 and about 16:1. In a more preferred embodiment, the bromoxynil and the PPO inhibitor are present in a ratio between about 8:1 and about 16:1. In one embodiment the bromoxynil and the PPO inhibitor are present in a ratio of about 5:1. In one embodiment the bromoxynil and the PPO inhibitor are present in a ratio of about 8:1. In one embodiment the bromoxynil and the PPO inhibitor are present in a ratio of about 10:1. In one embodiment the bromoxynil and the PPO inhibitor are present in a ratio of about 16:1. These can be commercial formulations that are tank mixed at the time of application, or a suitable premix formulation. Suitable premix formulations include, without limitation, suspension concentrate (SC) and emulsifiable concentrate (EC). In a further aspect, the agricultural formulation or tank mix contains an additional herbicide. The additional herbicide can be selected, without limitation, from atrazine, glyphosate, glufosinate, pyroxasulfone, dicamba, diflufenzopyr, nicosulfuron, salts thereof, or mixtures of two or more thereof. In one aspect the additional herbicide is glyphosate.

The average size or maturity of the volunteer crop weed is indicated by the leaf stage of the plant (total number of leaves on the plant), and in one embodiment, is 1 to about 6 leaves, or more. In one embodiment the average crop weed is in an early leaf stage having about 2 to about 4 leaves. In other embodiments, the average crop weed is in an intermediate leaf stage having 4 to about 6 leaves, or greater than 4 leaves, or about 5 to about 6 leaves or more. In another embodiment, the average crop weed is in a late stage having greater than 6 leaves. For the purposes of the present disclosure, these latter stages, with 4 leaves or more, are considered more mature weeds.

In one embodiment the applied composition is effective to control more mature volunteer crop weeds, with more mature weeds being indicated by the 4-6 leaf stage, or larger. In one embodiment volunteer crop weeds at about the 2-6 leaf stage are effectively controlled. In one embodiment volunteer crop weeds at about the 2-4 leaf stage are effectively controlled. In another embodiment volunteer crop weeds at about the more mature 4-6 leaf stage are effectively controlled. In yet another embodiment volunteer crop weeds at about the more mature 4-6 leaf or greater stage are effectively controlled. In one embodiment the volunteer crop weeds comprise canola or genetically modified canola, or glyphosate- or glufosinate-resistant canola.

The volunteer crop weeds can be selected from the group consisting of canola, genetically modified canola, soybean and genetically modified soybean. Other susceptible weed species include, without limitation, waterhemp, lambsquarters, velvetleaf, palmer amaranth, pigweed, morning glory, cocklebur, ragweed, broadleaf signalgrass, foxtail, crabgrass, volunteer soybean, nutsedge, Egyptian crowfoot grass, fumitory, denticulate medick, lesser swine cress, brown beetle grass, jungle grass, tendla, false amaranth, common purslane and field bindweed. In one embodiment the crop is selected from the group consisting of genetically modified and non-modified corn, wheat, oat, rye, soybean, cotton, flax, jute, rape, canola, linseed, sesame, safflower, sunflower, clover, beet, sugar beet, sorghum, millet, rice, peanut, pea, bean, cucumber, pepper, melon, cabbage, onion, squash, lettuce, asparagus, eggplant, tomato, tobacco, flower seed and turfgrass. In another embodiment, the crop to be treated is wheat, oat, rye, soybean, cotton, flax, jute, or rape.

In another embodiment, the crop weed is selected from the group consisting of canola, genetically modified canola, and mixtures thereof. In a specific embodiment the crop weed is selected from the group consisting of canola, genetically modified canola, and mixtures thereof, and the volunteer crop weed is genetically modified canola. In one embodiment the crop weed is glyphosate- or glufosinate-resistant canola.

In another embodiment of the method the herbicidal composition is applied to a field as a burn down treatment in order to eliminate the emerged weeds, including volunteer crop weeds, prior to seeding the desired crop, for example, canola or flax. The seeded canola crop can be genetically modified or a non-modified variety. The volunteer crop weeds can comprise canola, either genetically modified, a non-modified variety or combinations thereof.

The compositions and tank mixes of the present disclosure can additionally comprise further crop protection agents, selected from the group consisting of fungicides, insecticides, nematocides, plant growth regulators, herbicides other than bromoxynil and PPO herbicides, and fertilizers. In one embodiment the composition comprises a tank mix of formulated bromoxynil and a formulated protoporphyrinogen oxidase (PPO) inhibitor. In one embodiment the PPO inhibitor is carfentrazone-ethyl. In one embodiment the tank mix further comprises glyphosate or glufosinate. In a preferred embodiment the tank mix further comprises glyphosate.

In one embodiment the applied rate of bromoxynil and/or the applied rate of the protoporphyrinogen oxidase inhibitor is less than the registered application rate for control of the crop represented by the volunteer crop weed. In one embodiment the applied rate of bromoxynil and the applied rate of carfentrazone-ethyl are each half of their registered rates for control of the crop represented by the volunteer crop weed. Carfentrazone-ethyl is labeled or registered at a use rate of 18 gai/ha to control volunteer canola with no residual carry over that could potentially damage the establishing canola crop. Bromoxynil is registered at a use rate of 280 gai/ha to control volunteer canola, also with no residual carry over that could potentially damage an establishing canola crop seeded post-treatment.

In at least one aspect of the present invention, the inventors conducted Field Trials in Georgia, US, in 2013, and in 2014 in Canada and have successfully shown that a tank mix of carfentrazone at 9 gai/ha and bromoxynil at 140 gai/ha gives control of glyphosate- or glufosinate-resistant canola significantly greater than either product alone at its registered use rate. Thus, in one embodiment it has been demonstrated that one-half of the registered use rates of both carfentrazone-ethyl and bromoxynil when tank mixed provide good control of volunteer canola greater than either product alone at the full registered use rate. See Examples.

In one embodiment, the control of the volunteer crop weed is effective through at least 21 days post-treatment, preferably at least 35 days post treatment. In one embodiment of the method, the applied composition provides synergistic control of the volunteer crop weed.

Thus, another aspect of the invention is directed to a synergistic herbicidal composition comprising bromoxynil and a protoporphyrinogen oxidase inhibitor (PPO) in a ratio between about 4:1 and about 16:1, preferably about 8:1 to about 16:1, wherein application of an effective amount of the synergistic herbicidal composition selectively controls volunteer crop weeds in a crop. In one embodiment the synergistic herbicidal composition further comprises glyphosate or glufosinate. In one embodiment the PPO inhibitor is selected from the group consisting of carfentrazone, carfentrazone-ethyl, sulfentrazone, fluthiacet-methyl, saflufenacil, and mixtures of two or more thereof. In one embodiment the protoporphyrinogen oxidase inhibitor comprises carfentrazone-ethyl. In one embodiment the synergistic herbicidal composition comprises carfentrazone-ethyl and further comprises glyphosate.

In another aspect of the invention, mixtures containing carfentrazone-ethyl, glyphosate and bromoxynil octanoic acid ester exhibit a synergistic effect in control of volunteer canola when compared to the control of canola using mixtures of carfentrazone-ethyl/glyphosate and bromoxynil octanoic acid ester/glyphosate. In one embodiment, the synergy is maintained for at least 5, 7, 10, 14, 19, 21, 35, or 45 days after planting. In another embodiment, the synergistic effect is provided for mature stage canola weeds for at least 5, 7, 10, 14, 19, 21, 35, or 45 days after planting. In a more preferred embodiment, the synergistic effect is provided for volunteer, genetically modified or glyphosate resistant canola having at least 6 leaves.

The compositions of the present disclosure can also include a preservative. Suitable preservatives include, but are not limited to, $C_{12}$ to $C_{15}$ alkyl benzoates, alkyl p-hydroxybenzoates, aloe vera extract, ascorbic acid, benzalkonium chloride, benzoic acid, benzoic acid esters of $C_9$ to $C_{15}$ alcohols, butylated hydroxytoluene, butylated hydroxyanisole, tert-butylhydroquinone, castor oil, cetyl alcohols, chlorocresol, citric acid, cocoa butter, coconut oil, diazolidinyl urea, diisopropyl adipate, dimethyl polysiloxane, DMDM hydantoin, ethanol, ethylenediaminetetraacetic acid, fatty acids, fatty alcohols, hexadecyl alcohol, hydroxybenzoate esters, iodopropynyl butylcarbamate, isononyl iso-nonanoate, jojoba oil, lanolin oil, mineral oil, oleic acid, olive oil, parabens, polyethers, polyoxypropylene butyl ether, polyoxypropylene cetyl ether, potassium sorbate, propyl gallate, silicone oils, sodium propionate, sodium benzoate, sodium bisulfite, sorbic acid, stearic fatty acid, sulfur dioxide, vitamin E, vitamin E acetate and derivatives, esters, salts and mixtures thereof. Preferred preservatives include sodium o-phenylphenate, 5-chloro-2-methyl-4-isothiazolin-3-one, 2-methyl-4-isothiazolin-3-one, and 1,2-benisothiazolin-3-one.

Definitions

As used in this application and unless otherwise indicated the term "herbicide" refers to a compositional mixture that is produced, sold, or used in a field in order to kill or otherwise inhibit unwanted plants such as, but not limited to, deleterious or annoying weeds, broadleaf plants, grasses, and sedges; and can be used for crop protection, edifice protection or turf protection. The term "herbicide" includes the end-use herbicidal product. This composition can be a pure compound, a solution of chemical compounds, a mixture of chemical compounds, an emulsion, a suspension, a solid-liquid mixture, or a liquid-liquid mixture. The term "herbicide" also refers to the product that passes through the commercial channels from the manufacturer to the ultimate end user who can either apply the herbicide to the affected field as sold, or mix it with other excipients.

The term "weed" means and includes any plant which grows where it is not wanted, including volunteer crop plants or insecticide resistant plants.

The term "effective" or "herbicidally effective amount" means an amount necessary to produce an observable herbicidal effect on unwanted plant growth, including one or more of the effects of necrosis, death, growth inhibition, reproduction inhibition, inhibition of proliferation, and removal, destruction, or otherwise diminishing the occurrence and activity of unwanted plants.

The term "herbicidally active ingredient" means the active ingredient in the herbicide that causes the herbicide to prevent, destroy, repel or mitigate any weed. Other ingredients of the herbicide that are not herbicidally active ingredients are excipients that aid in forming, storing, or delivering herbicidally active ingredient to the target. Examples of excipients in the present embodiment include, without limitation, an organic liquid in which herbicidally active ingredient is dissolved, a polyurea shell, a water-soluble polymer, and one or more salts.

The definition of the term "herbicidal composition" refers to a herbicide, and in addition, to any composition that comprises a herbicidally active ingredient. This composition can be a solution or a mixture. Further, the definition of the term "herbicidal composition" also refers to a product intended for use in manufacturing, or any product intended for formulation or repackaging into other agricultural products.

As used herein, the terms "synergy" and "synergistic", or the phrase "in a synergistic manner", refer to the in vivo interaction of two or more biologically active compounds, in the present case bromoxynil and a PPO inhibitor, so that their combined effect when administered together is greater than the sum of the effects observed when each is administered individually. That is, the herbicidal effect of administering the combination of bromoxynil and a PPO inhibitor as disclosed above, is greater than the sum of the herbicidal effects of administering bromoxynil alone and the PPO inhibitor alone at their use rates. In this way the applied rate of the herbicidal combination can be lower than the registered use rates, thereby reducing the total chemical burden on the field to which such a combination is applied. In the present disclosure, the method of Colby is used to establish synergism (see Colby, S. R., "Calculating Synergistic and Antagonistic Responses of Herbicide Combinations", *Weeds* 1967, 15, pg 20-22, which is incorporated herein by reference). Thus, the presence of a synergistic effect between the two active ingredients is established with the aid of the Colby equation: $E=X+Y-(XY/100)$. See the Examples presented below. In these examples the volunteer canola weed is genetically modified to be tolerant to glyphosate (ROUNDUP READY® canola, Monsanto), therefore the glyphosate present in the applied typical burn down formulations should have no effect on this volunteer crop weed species. Further, calculation of synergy using the Colby equation zeroes out any effect of glyphosate, since it is present at the same rate in all applications.

As used herein, the terms "labeled use rate" or "registered use rate" or "labeled application rate" or "registered application rate" as applied to herbicidal compositions refer to the rate of application to a field containing crops and/or weeds, which rate has been established by the agrochemical industry, as reflected in Environmental Protection Agency (EPA) regulations, to be appropriate for control of the indicated weed species. The registered use rate is reflected on the commercial formulation packaging in an appropriate label. Thus, one-half the registered use rate would indicate application of only half of the labeled rate of a herbicidal formulation, with respect to the gai applied.

The following examples serve only to illustrate the invention and should not be interpreted as limiting the scope of the invention in any way, since further modifications encompassed by the disclosed invention will be apparent to those skilled in the art. All such modifications are deemed to be within the scope of the invention as disclosed in the present specification and claims.

EXAMPLES

Example 1

Control of Glyphosate-Resistant Canola with Mixtures of Glyphosate, Carfentrazone-ethyl and Bromoxynil Test plots located in Winnipeg, Manitoba, Canada (4 replicates for each rate, 13 $m^2$ each) were seeded with ROUNDUP READY® canola (RR® canola). Once the canola emerged and was at the 2 to 4-leaf stage, the plots were sprayed with the test at a spray volume of 100 L/ha. The test plots were evaluated for % control of canola as compared to untreated control plots. In order to provide a measure of the effectiveness of a herbicide's performance weed control ratings were based on visual observations of the presence or absence of canola. Ratings were based on a 0 to 100 rating system, where 0 equals no control and 100 equals complete control, which generally makes use of direct-percentage figures. In this system the standard basis for comparison is an untreated check. Counts are made of canola found in the untreated area of the study. This provides a basis to give a precise representation of both canola in the untreated plots and degree of control provided by various chemical treatments.

The presence of a synergistic effect between the two active ingredients is established with the aid of the Colby equation (see Colby, S. R., "Calculating Synergistic and Antagonistic Responses of Herbicide Combinations", *Weeds* 1967, 15, pg 20-22): $E=X+Y-(XY/100)$. In the present example, X is represented by a certain mixture of glyphosate (ROUNDUP WEATHERMAX® Herbicide from Monsanto) and carfentrazone-ethyl (AIM® EC Herbicide from FMC Corporation) and Y is a mixture of glyphosate (ROUNDUP WEATHERMAX® Herbicide from Monsanto) and bromoxynil octanoic acid ester (PARDNER® Herbicide from Bayer CropScience).

Using the method of Colby, the presence of a synergistic interaction between two active ingredients is established by first calculating the expected activity, 'E', of the mixture based on activities of the two components applied alone. In the equation above, 'X' is the herbicidal activity in percentage control of glyphosate and carfentrazone-ethyl applied as a mixture at rate 'x'. The 'Y' term is the herbicidal activity of glyphosate and bromoxynil applied as a mixture at rate 'y'. The equation calculates 'E', the herbicidal activity of the mixture of 'X' at rate 'x' with 'Y' at rate 'y'. If 'E' is lower than the observed activity, synergy is present. If the herbicidal effect is strictly additive and no interaction has occurred, 'E' will be equal to or higher than the observed activity. Tables 1A and 1B below summarize (average of 4 replicates) the % control of canola and the expected verses observed % control of mixtures of carfentrazone-ethyl, glyphosate and bromoxynil octanoic acid ester in two trials.

TABLE 1A

% Control of RR® Canola Trial 1, Manitoba, Canada

| Treatment Rate | % Control of Canola, 2-4 leaf stage | | |
|---|---|---|---|
| | 8 DAT | 18 DAT | 35 DAT |
| AIM® (9 gai/ha) + ROUNDUP WEATHERMAX® (450 gai/ha) | 65.5 | 63.5 | 48.5 |
| AIM® (18 gai/ha) + ROUNDUP WEATHERMAX® (450 gai/ha) | 78.5 | 76.5 | 65.0 |
| PARDNER® (140 gai/ha) + ROUNDUP WEATERMAX® (450 gai/ha) | 76.3 | 75.8 | 58.3 |
| AIM® (9 gai/ha) + ROUNDUP WEATHERMAX® (450 gai/ha) + PARDNER® (140 gai/ha) | Expected = 91.8 Observed = 91.8 | Expected = 91.1 Observed = 95.0 | Expected = 78.5 Observed = 89.5 |
| AIM® (18 gai/ha) + ROUNDUP WEATHERMAX® (450 gai/ha) + PARDNER® (140 gai/ha) | Expected = 94.9 Observed = 97.0 | Expected = 94.3 Observed = 97.8 | Expected = 85.4 Observed = 97.3 |

TABLE 1B

% Control of RR® Canola Trial 2, Manitoba, Canada

| Treatment Rate | % Control of Canola, 2-4 leaf stage | | |
|---|---|---|---|
| | 4 DAT | 12 DAT | 19 DAT |
| AIM® (9 gai/ha) + ROUNDUP WEATHERMAX® (450 gai/ha) | 45.0 | 56.0 | 58.8 |
| AIM® (18 gai/ha) + ROUNDUP WEATHERMAX® (450 gai/ha) | 40.5 | 62.5 | 68.5 |
| PARDNER® (140 gai/ha) + ROUNDUP WEATERMAX® (450 gai/ha) | 47.8 | 58.3 | 66.3 |
| AIM® (9 gai/ha) + ROUNDUP WEATHERMAX® (450 gai/ha) + PARDNER® (140 gai/ha) | Expected = 71.3 Observed = 78.5 | Expected = 81.7 Observed = 91.8 | Expected = 86.1 Observed = 93.3 |
| AIM® (18 gai/ha) + ROUNDUP WEATHERMAX® (450 gai/ha) + PARDNER® (140 gai/ha) | Expected = 68.9 Observed = 76.8 | Expected = 84.4 Observed = 93.8 | Expected = 89.4 Observed = 94.3 |

As can be seen from the Tables above, mixtures containing carfentrazone-ethyl, glyphosate and bromoxynil exhibit a synergistic effect in control of canola when compared to mixtures of carfentrazone-ethyl/glyphosate and bromoxynil octanoic acid ester/glyphosate.

Example 2

Control of Glyphosate-Resistant Canola with Mixtures of Glyphosate, Carfentrazone-ethyl and Bromoxynil Test plots located in Sparks Ga., USA (4 replicates for each rate, 13 m² each) were seeded with ROUNDUP READY® canola (RR® canola). Once the canola emerged and was at the 1 to 3-leaf or 4 to 6 leaf stage, the plots were sprayed with the test at a spray volume of 100 L/ha. The test plots were evaluated for % control of canola as compared to untreated control plots. In order to provide a measure of the effectiveness of a herbicide's performance weed control ratings were based on visual observations of the presence or absence of canola. Ratings were based on a 0 to 100 rating system, where 0 equals no control and 100 equals complete control, which generally makes use of direct-percentage figures.

In this system the standard basis for comparison is an untreated check. Counts are made of canola found in the untreated area of the study. This provides a basis to give a precise representation of both canola in the untreated plots and degree of control provided by various chemical treatments. The trials were read at 7, 14 and 21 days after treatment (DAT). The presence of a synergistic effect between the two active ingredients is established with the aid of the Colby equation (see Colby, S. R., "Calculating Synergistic and Antagonistic Responses of Herbicide Combinations", *Weeds* 1967, 15, pg 20-22): $E=X+Y-(XY/100)$. In the present example, X is represented by a certain mixture of glyphosate (ROUNDUP WEATHERMAX® Herbicide from Monsanto) and carfentrazone-ethyl AIM® EC Herbicide from FMC Corporation) and Y is a mixture of glyphosate (ROUNDUP WEATHERMAX® Herbicide from Monsanto) and bromoxynil octanoic acid ester (MAESTRO® 2EC Herbicide from Nufarm).

Table 2 below summarizes (average of 4 replicates) the % control of canola and the expected verses observed % control of mixtures of carfentrazone-ethyl, glyphosate and bromoxynil octanoic acid ester in two trials.

mixture of the present invention exhibits up to 3 times more control when compared to individual mixtures of carfentrazone-ethyl/glyphosate and bromoxynil octanoic acid ester/glyphosate.

TABLE 2

% Control of RR ® Canola, Georgia, USA

| | % Control of Canola | | | | | |
|---|---|---|---|---|---|---|
| Treatment Rate | 7 DAT 1-3 leaf | 7 DAT 4-6 leaf | 14 DAT 1-3 leaf | 14 DAT 4-6 leaf | 21 DAT 1-3 leaf | 21 DAT 4-6 leaf |
| AIM ® (9 gai/ha) + ROUNDUP WEATHERMAX ® (450 gai/ha) | 5 | 0 | 22 | 0 | 36 | 1 |
| AIM ® (18 gai/ha) + ROUNDUP WEATHERMAX ® (450 gai/ha) | 16 | 0 | 49 | 1 | 79 | 5 |
| AIM ® (27 gai/ha) + ROUNDUP WEATHERMAX ® (450 gai/ha) | 20 | 1 | 54 | 7 | 81 | 12 |
| MAESTRO ® (140 gai/ha) + ROUNDUP WEATERMAX ® (450 gai/ha) | 27 | 0 | 78 | 5 | 78 | 10 |
| MAESTRO ® (280 gai/ha) + ROUNDUP WEATERMAX ® (450 gai/ha) | 46 | 0 | 96 | 15 | 76 | 42 |
| AIM ® (9 gai/ha) + ROUNDUP WEATHERMAX ® (450 gai/ha) + MAESTRO ® (140 gai/ha) | Expected 31 Observed 59 | Expected 0 Observed 1 | Expected 83 Observed 94 | Expected 5 Observed 12 | Expected 86 Observed 95 | Expected 11 Observed 41 |
| AIM ® (9 gai/ha) + ROUNDUP WEATHERMAX ® (450 gai/ha) + MAESTRO ® (280 gai/ha) | Expected 49 Observed 85 | Expected 0 Observed 11 | Expected 97 Observed 98 | Expected 15 Observed 42 | Expected 85 Observed 87 | Expected 43 Observed 53 |
| AIM ® (18 gai/ha) + ROUNDUP WEATHERMAX ® (450 gai/ha) + MAESTRO ® (140 gai/ha) | Expected 39 Observed 80 | Expected 0 Observed 19 | Expected 89 Observed 97 | Expected 6 Observed 33 | Expected 95 Observed 99 | Expected 15 Observed 68 |
| AIM ® (18 gai/ha) + ROUNDUP WEATHERMAX ® (450 gai/ha) + MAESTRO ® (280 gai/ha) | Expected 55 Observed 85 | Expected 0 Observed 21 | Expected 98 Observed 99 | Expected 16 Observed 53 | Expected 95 Observed 99 | Expected 45 Observed 76 |
| AIM ® (27 gai/ha) + ROUNDUP WEATHERMAX ® (450 gai/ha) + MAESTRO ® (140 gai/ha) | Expected 42 Observed 72 | Expected 1 Observed 20 | Expected 90 Observed 99 | Expected 12 Observed 50 | Expected 96 Observed 91 | Expected 21 Observed 71 |
| AIM ® (27 gai/ha) + ROUNDUP WEATHERMAX ® (450 gai/ha) + MAESTRO ® (280 gai/ha) | Expected 57 Observed 91 | Expected 1 Observed 39 | Expected 98 Observed 100 | Expected 21 Observed 75 | Expected 95 Observed 100 | Expected 49 Observed 83 |

As can be seen from Table 2, above, mixtures containing carfentrazone-ethyl, glyphosate and bromoxynil octanoic acid ester exhibit a synergistic effect in control of canola when compared to the control of canola using mixtures of carfentrazone-ethyl/glyphosate and bromoxynil octanoic acid ester/glyphosate. In fact, in some tests the three-way Although the invention herein has been described with reference to particular embodiments, it is to be understood that these embodiments are merely illustrative of the principles and applications of the present invention. It is therefore to be understood that numerous modifications may be made to the illustrative embodiments and that other arrange-

What is claimed is:

1. A method of selectively controlling glyphosate- or glufosinate-resistant volunteer crop weeds in a desired crop, comprising applying to volunteer crop weeds a herbicidally effective amount of a composition comprising bromoxynil or bromoxynil octanoic acid ester plus glyphosate or glufosinate, plus a protoporphyrinogen oxidase inhibitor, wherein said volunteer crop weeds are selected from the group consisting of canola, genetically modified canola and mixtures thereof and wherein combinations of the protoporphyrinogen oxidase inhibitor plus glyphosate or glufosinate plus bromoxynil or bromoxynil octanoic acid ester exhibit a synergistic effect in control of the canola when compared to combinations of protoporphyrinogen oxidase inhibitor plus glyphosate or glufosinate and combinations of bromoxynil or bromoxynil octanoic acid ester plus glyphosate or glufosinate.

2. The method of claim 1, wherein said protoporphyrinogen oxidase inhibitor is selected from the group consisting of carfentrazone, sulfentrazone, fluthiacet-methyl, saflufenacil, and mixtures of two or more thereof.

3. The method of claim 1, wherein said protoporphyrinogen oxidase inhibitor comprises carfentrazone.

4. The method of claim 1, wherein said volunteer crop weeds are in the 1-6 leaf stage.

5. The method of claim 1, wherein said desired crop is selected from the group consisting of genetically modified and non-modified corn, wheat, oat, rye, soybean, cotton, flax, jute, rape, canola, linseed, sesame, safflower, sunflower, clover, beet, sugar beet, sorghum, millet, rice, peanut, pea, bean, cucumber, pepper, melon, cabbage, onion, squash, lettuce, asparagus, eggplant, tomato, tobacco, flower seed and turfgrass.

6. The method of claim 1, wherein said desired crop is selected from the group consisting of canola, genetically modified canola, and mixtures thereof.

7. The method of claim 1, wherein said composition comprises a tank mix of formulated bromoxynil and a formulated protoporphyrinogen oxidase inhibitor.

8. The method of claim 7, wherein said protoporphyrinogen oxidase inhibitor is carfentrazone-ethyl.

9. The method of claim 1, wherein an applied rate of bromoxynil and/or an applied rate of protoporphyrinogen oxidase inhibitor is less than registered application rate for control of the volunteer crop weed.

10. The method of claim 8, wherein an applied rate of bromoxynil and an applied rate of carfentrazone-ethyl are each half of their registered rates for control of the volunteer crop weed.

11. The method of claim 1, wherein control of said volunteer crop weed is effective
through at least 21 days post treatment.

12. The method of claim 4, which is effective to control mature volunteer crop weeds.

13. A herbicidal composition comprising a synergistically effective amount of bromoxynil or bromoxynil octanoic acid ester, a plus protoporphyrinogen oxidase inhibitor, plus a glyphosate or a glufosinate, wherein the herbicidal composition is effective to selectively control volunteer crop weeds in a crop, and wherein said volunteer crop weeds are selected from the group consisting of canola, genetically modified canola and mixtures thereof and wherein combinations of the protoporphyrinogen oxidase inhibitor plus glyphosate or glufosinate plus bromoxynil or bromoxynil octanoic acid ester exhibit a synergistic effect in control of canola when compared to combinations of protoporphyrinogen oxidase inhibitor plus glyphosate or glufosinate and combinations of bromoxynil or bromoxynil octanoic acid ester plus glyphosate or glufosinate.

14. The herbicidal composition of claim 13, wherein said protoporphyrinogen oxidase inhibitor is selected from the group consisting of carfentrazone, sulfentrazone, fluthiacet-methyl, saflufenacil, and mixtures of two or more thereof.

15. The herbicidal composition of claim 13, wherein said protoporphyrinogen oxidase inhibitor comprises carfentrazone.

* * * * *